United States Patent [19]

Crandall

[11] Patent Number: 4,517,461
[45] Date of Patent: May 14, 1985

[54] CARBON ISOTOPE ANALYSIS OF HYDROCARBONS

[76] Inventor: John A. Crandall, c/o Phillips Petroleum Co., Bartlesville, Okla. 74004

[21] Appl. No.: 445,312

[22] Filed: Nov. 29, 1982

[51] Int. Cl.³ .............................................. B01D 59/44
[52] U.S. Cl. ................................... 250/282; 250/281; 422/54
[58] Field of Search ........................ 250/282, 281, 288; 73/23.1; 422/54

[56] References Cited

U.S. PATENT DOCUMENTS

| | | | |
|---|---|---|---|
| 3,084,012 | 4/1963 | Jenckel | 346/49 |
| 3,398,505 | 8/1968 | Llewellyn | 55/16 |
| 3,405,549 | 10/1968 | Finley | 77/23.1 |
| 3,421,292 | 1/1969 | Llewellyn | 55/158 |
| 3,429,105 | 2/1969 | Llewellyn | 55/158 |
| 3,455,092 | 7/1969 | Llewellyn | 55/158 |
| 3,466,597 | 9/1969 | Bray et al. | 23/230 |
| 3,563,083 | 2/1971 | Benz | 73/23.1 |
| 3,566,674 | 3/1971 | Talroze et al. | 73/23.1 |
| 3,589,171 | 6/1971 | Haley | 73/23.1 |
| 3,592,044 | 7/1971 | Green | 73/23.1 |
| 3,641,339 | 2/1972 | McCormick | 250/41.9 G |
| 3,686,923 | 8/1972 | Favre | 73/23.1 |
| 3,712,111 | 1/1973 | Llewellyn | 73/23.1 |
| 3,786,249 | 1/1974 | Anbar | 250/41.9 G |
| 3,860,393 | 1/1975 | Campen | 23/230 R |
| 4,111,554 | 9/1978 | Colin et al. | 73/23.1 |
| 4,112,297 | 9/1978 | Miyagi et al. | 250/288 |
| 4,408,125 | 10/1983 | Meuzelaar | 250/288 |

OTHER PUBLICATIONS

"Improved Double Detection Gas Chromatograph Mass Spec. Interface for the Analysis of Complex Organic Mixtures", by F. Brumer et al. Anal. Chem. vol. 45, No. 6, May 1973, pp. 1002–1006.
"Mass Spectrometric GC" article, C & E News, Aug. 2, 1982.

Primary Examiner—Alfred E. Smith
Assistant Examiner—Richard Hanig

[57] ABSTRACT

Method and apparatus are provided for analysis of a sample of matter for at least one isotopic constituent of the sample. The method involves introduction of a sample containing an isotope of interest into an analytical detector operative to convert the sample into a product analyzable by a mass spectrometer and to detect a property of the sample representative of the quantity of at least one of its constituents, and passing the conversion product from the detector to a mass spectrometer operative to detect the isotopic ratio of interest. The method optionally includes passing the sample or a source material through a chromatograph column for separation into suitable fractions. The apparatus includes an appropriate analytical detector and a mass spectrometer with optional chromatography column. The method and instrument are particularly suited for analysis of oil-related samples such as crude oil fractions, natural gas, soil gas and oil shale as a tool in oil prospecting.

19 Claims, 3 Drawing Figures

CARBON ISOTOPE ANALYSIS OF HYDROCARBONS

BACKGROUND OF THE INVENTION

This invention relates to analytical instruments and methods. In one aspect, it relates to the analysis of a hydrocarbon sample to determine the isotopic carbon content. In another aspect, the invention relates to methods and instruments for geochemical oil prospecting.

Modern methods of oil exploration involve the use of a combination of seismic and geochemical prospecting methods. Geochemical prospecting methods have developed from an understanding of the ways in which petroleum originated and relocated in, or migrated to, a particular location. It is known that petroleum has an organic origin and developed from the remains of living organisms deposited into sediments. The sediments were buried and the action of temperature and pressure over time generated petroleum from the deposited organic matter. It is believed that petroleum found in reservoirs today has often migrated to the reservoir from the original location of petroleum generation.

In exploring for oil, it is useful to know the locations of such oil-generating formations, which can then be used in combination with seismic and geological data from the region to predict the locations of other oil-bearing reservoirs to which oil may have migrated from a common source formation. If information on the type of source rock can be obtained from petroleum or other type of geological sample, this information can be used in finding the source formation and in targeting future drilling at this formation and proximal traps. In addition, assessment of source rock type from known reservoir samples can enable determination of whether a common source for the reservoirs is involved. Different sources may indicate possible additional undiscovered reservoirs in proximal locations.

One geochemical oil prospecting method involves the study of carbon-containing geological samples from an oil-bearing region to determine the relative amounts of carbon isotopes in the sample. In such a method, it is common to convert the carbon in the sample to carbon dioxide and then to measure by means of an isotope ratio mass spectrometer or other instrument the ratio of $C^{13}$ to $C^{12}$ in the sample.

It is thus important to be able to quantitatively convert the carbon in a sample to carbon dioxide. This can be done by combustion of the sample in an oxygen-rich atmosphere. For the type of geochemical methods which are presently used to study samples, it is desirable to study the carbon isotopic ratio of relatively small samples, say on the order of 2 cubic centimeters. Conventional methods for such an analysis, however, require relatively large samples in the order of 50 to 100 cc to produce accurate, reproducible results. The use of such large samples has the disadvantages of requiring a relatively long time to run an analysis, of requiring amounts of samples of material which are sometimes difficult to obtain or retain, and requiring large combustion apparatus in addition to the mass spectrometer. Certain conventional instruments also produce inconsistent results due to incomplete conversion of carbon to carbon dioxide.

It is therefore an object of this invention to provide apparatus and method for analyzing a sample of matter.

It is a further object to provide a simple and rapid method for determining the isotopic carbon ratio of a hydrocarbon sample.

It is a further object to provide means for determining the source rock potential of a geological sample.

SUMMARY OF THE INVENTION

According to the invention, a method is provided whereby a sample of matter containing an isotope of interest is quantitatively converted by combustion to a combustion product containing the isotope of interest, which is then analyzed for a property related to isotope abundance, such as isotope ratio. The conversion of the sample is carried out by means of a device which is capable of combusting small samples and simultaneously determining a property of the sample. Such a device is suitably a flame ionization detector or flame photometric detector. The analysis for isotopic ratio is suitably carried out with an isotope ratio mass spectrometer. According to one embodiment of the invention, a sample is separated into at least two constituents by means such as a gas chromatograph prior to combustion of at least one separated constituent and subsequent isotopic analysis of the combustion product.

Also according to the invention, apparatus is provided comprising means for converting the small sample of matter to a combustion product and means in flow communication therewith to quantitatively analyze an isotope of interest in the thus-converted sample. The invention apparatus can optionally include means to separate, such as by boiling points, the sample into at least two components. A suitable apparatus could include, for example, means such as a flame ionization detector for conversion of the carbon in a sample to carbon dioxide and essentially simultaneous determination of a property of the sample and, in flow communication therewith, means such as a mass spectrometer to determine the $C^{13}/C^{12}$ ratio of the sample. Optionally, the apparatus could include means such as a gas chromatography column for separating from a sample at least one component of interest for combustion and isotopic carbon analysis.

The described invention method and apparatus are particularly suited for the study of natural fluids such as crude oil and natural gas and geological samples such as shale, as a tool for geochemical oil prospecting. They offer the advantages of high combustion efficiency, ability to analyze small samples, short analysis time, and simultaneous hydrocarbon quantitative analysis and combustion.

DETAILED DESCRIPTION OF THE INVENTION

The invention method in one embodiment includes the conversion of hydrocarbon in a sample to carbon dioxide. This can be accomplished by combustion of the hydrocarbon in an excess of oxygen. For small samples of a material such as natural gas, this is most preferably accomplished by passage of the sample or components thereof through a flame ionization detector, which is an instrument conventionally used for quantitative analysis of a hydrocarbon component of a sample by combustion of the sample components in a hydrogen-rich flame and detection of selected ions produced by the combustion.

In the invention method, the effluent from the flame ionization detector, which will include carbon dioxide and water, is analyzed for the relative amounts of isotopes of carbon present. This can be accomplished by means of an isotope ratio mass spectrometer. The effluent can be treated prior to carbon isotope analysis for removal of undesired components, which will generally include water and inert gases.

Depending upon the type of sample to be analyzed, the method can involve a separation step for obtaining a desired constituent or group of constituents from the sample. The separation of a gaseous sample can be effected using gas chromatography, from which the desired constituents can be passed to the flame ionization detector and to the mass spectrometer.

The samples which can be analyzed by the invention method include any carbon-containing material which can be oxidized with good efficiency to carbon dioxide. Hydrocarbon materials are particularly suitable. For geochemical oil prospecting, geological samples such as petroleum, natural gas, soil gas, shale, coal and constituents of these can be analyzed.

The method of the invention is designed particularly for analyses of small samples of matter. Generally, the size of solid samples will be in the range of about 1 mg to about 200 mg processed through a pyrolytic instrument to release entrapped gases, while gaseous samples passed to the conversion device will range in size from about 1 cc to about 25 cc at STP. Quantitative conversion of the component of interest is desired, with about 95% efficiency possible treating a hydrocarbon sample in a flame ionization detector.

Figure 1:
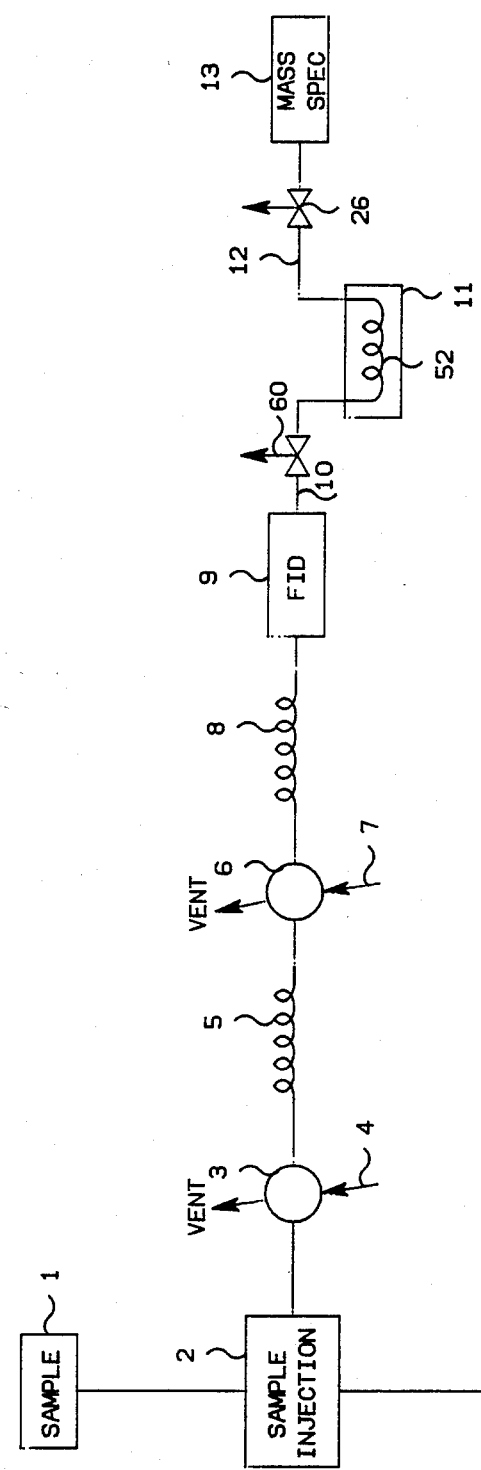
FIG. 1 is a schematic diagram of the method and apparatus according to one embodiment of the invention.

The apparatus of the invention can best be described by reference to the drawings. FIG. 1 illustrates in schematic form the invention instrument with accompanying inlet system for receiving the sample. Not shown is a microprocessor for automatic control of the process and evaluation of data, conventionally associated with the mass spectrometer. In practical application, such an instrument would be used for the analysis of geologically-significant samples such as companion gases or liquids from a drilling site. The hydrocarbon component of soil can be separated by methods known in the art such as solvent extraction and pyrolysis.

The hydrocarbon sample in gas sample container 1 is introduced into the instrument via gas inlet injection system 2 and multiport valve 3. Sample injection system 2 can contain manometers for balancing pressures, a sample switching valve for inlet of unknown samples or reference gases, vacuum pumps and associated piping as is known to those skilled in the art. Reference gas container 51 contains a known concentration of components of interest used to calibrate the instrument.

An inert carrier gas such as helium is introduced via conduit 4 into multiport valve 3 and sweeps the sample contained in a measured sample loop into a first gas chromatograph column 5 containing suitable packing material such as Porasil ® packing. In column 5, separation of the hydrocarbon sample into components of high molecular weight (isobutane and heavier) and low molecular weight (propane and lighter) is made. The effluents from column 5 elute into multiport valve 6, known in the art as a backflush valve, and are swept by inert carrier gas introduced via conduit 7 to a second gas chromatograph column 8 containing suitable packing material such as Porasil ® packing. In column 8, the sample can be futher resolved into methane, ethane, ethylene, propane, carbon dioxide and other low molecular weight components. The thus separated components are fed individually into flame ionization detector (FID) 9. The FID combusts each hydrocarbon component with the exception of carbon dioxide, which passes the detector undetected and unreacted, and makes an individual quantitative analysis which can be recorded on a chart recorder such as Leeds & Northrup Model H.

The combustion products, which include carbon dioxide and water, of each component are passed via conduit 10 to cold trap 11, which is suitably a $\frac{1}{8}''$ glass spiral column 52 dynamically purged with $CO_2$-free helium and immersed in a slurry of iso-octane, liquid nitrogen and hexane. The cold trap is employed for differential freezing point separation of water from carbon dioxide, with water being retained in the trap. A valve 60 between the detector outlet and cold trap 11 permits venting of water from FID 9 when sample gases are not being collected. Valve 26 permits isolation of cold trap 11 from the mass spectrometer for water removal from the system.

Water is retained in cold trap 11 while carbon dioxide from each component is passed via conduit 12 to mass spectrometer 13, suitably a Micromass 903 triple collector mass spectrometer. The $C^{13}/C^{12}$ isotopic ratio is determined by the mass spectrometer for each hydrocarbon component. Mass spectrometer 13 includes a microcomputer for computation of the $C^{13}/C_{12}$ ratio and automatic control of the system.

Figure 2:
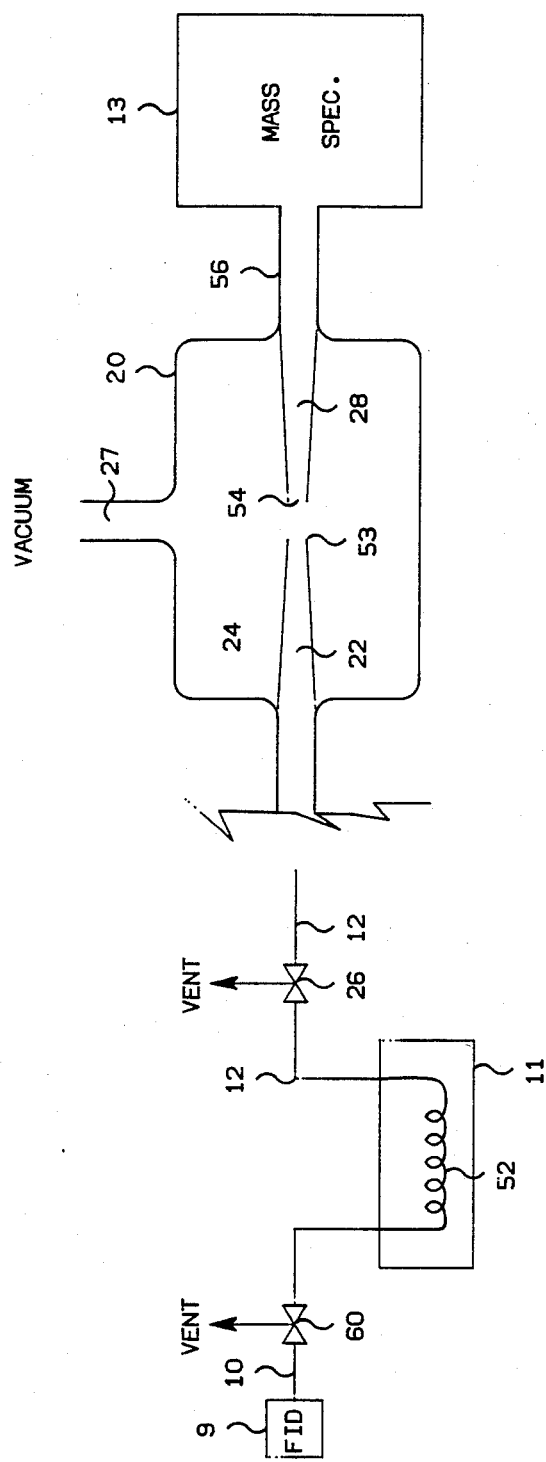
FIG. 2 is a schematic diagram of one embodiment of the invention method and apparatus showing the interface between the gas chromatograph and mass spectrometer.

FIG. 2 illustrates in schematic form an analytical instrument which includes means 20 to couple the combustion/detection device 9 to the mass spectrometer 13. The function of such a coupling device is to concentrate $CO_2$ relative to the carrier gas. Conduit 12 flows to $CO_2$ concentration means 20, which can be any device to enable the separation of $CO_2$ from the lighter carrier gas molecules and the passage of essentially carrier-free $CO_2$ to the mass spectrometer. An example of suitable $CO_2$ concentration means is a glass jet separator produced by Scientific Glass Engineering, Inc. The glass jet separator includes nozzle means 22 opening at outlet 53 into vacuum chamber 24. Coaligned and slightly displaced, suitably about 1 mm, from the nozzle means outlet is inlet 54 of funnel-shaped passage 28 extending into conduit 56 to mass spectrometer 13.

In operation, $CO_2$ gas from the cold trap mixed with inert carrier gas is injected into vacuum area 24 between nozzle outlet 53 and inlet 54. The gas stream spreads outward from the direction of travel of the stream, the spreading effect being greater for the lighter carrier gas molecules than for the heavier $CO_2$ molecules, which remain relatively concentrated in a stream from the nozzle means outlet to the inlet of the funnel-shaped passage. A larger opening, relative to the nozzle means outlet, for passage 28 accommodates for slight spreading of the $CO_2$ stream and permits the stream to enter the passage and to be introduced into the ionization chamber of the mass spectrometer. Most of the carrier gas molecules are dissipated into vacuum chamber 24 and can be removed therefrom via conduit 27.

It is within the scope of the invention to use any combustion/detection device for quantitative conversion of a small sample to combustion products suitable for analysis by mass spectrometry. Such devices can include but are not limited to flame ionization detectors and flame photometric detectors. A flame photometric detector can be used in place of the flame ionization detector in the systems described above for the analysis of, for example, sulfur-containing samples for isotopic ratio ($S^{34}/S^{32}$) determinations on $SO_2$.

The invention method and apparatus are particularly suited for analyses of petroleum-related characteristics of samples to assess their geological history as an aid in geochemical oil prospecting.

EXAMPLE I

The following run was performed to demonstrate the method and apparatus of the invention. The apparatus included a Perkin-Elmer 900 gas chromatograph, a Hewlett-Packard 9835 microcomputer and a Micromass 903 triple collector mass spectrometer. The sample gas inlet injection system for the gas chromatograph included a pressure regulator, two $\frac{1}{4}''$ ball valves, $\frac{1}{4}''$ stainless steel tubing, 6-port valve, a vacuum pump, and a 5 cc sample loop of $\frac{1}{8}''$ stainless steel tubing. The sample gas injection system, chromatographic columns, flame ionization detector, and coiled glass $CO_2$ trap were connected as illustrated in FIG. 1. The FID and mass spectrometer were not in flow communication for these runs.

Each of nine samples of Phillips Petroleum Company reference hydrocarbon standard from Borger Refinery was fed by means of the gas inlet system to the sample valve and sample loop. Helium carrier gas flow was 4.5 cc/min. The sample was passed through a first gas chromatography (GC) column in an oven maintained at 100° C. The GC column contained Porasil ® packing. Isobutane and heavier components of the sample were delayed in the column while methane, $CO_2$, propane, ethane and the like eluted through. Prior to elution of the low molecular weight components from the first column, the FID output valve was in the vent position to permit removal of water generated by the FID.

Upon elution of the low molecular weight components from the first column, the detector output valve was changed to the cold trap position. The eluted material was passed to the second chromatograph column of Porasil ® packing. After elution of the gases of interest from the first column, the backflush valve was switched to vent to flush the heavies from the first column.

The separated components from the second column were passed to the flame ionization detector in seriatim. In the detector the eluted hydrocarbon components were combusted in an oxygen/hydrogen atmosphere to form $CO_2$ and water, which were passed to a liquid nitrogen cold trap for condensation of the $CO_2$ and water.

After separation of $CO_2$ from the water by differential freezing using an iso-octane, liquid nitrogen and hexane slurry, the $CO_2$ was collected in a sample collection vessel and manually introduced into the mass spectrometer. Table I gives the results of isotopic analysis of the nine reference hydrocarbon samples analyzed for carbon dioxide from methane of each sample. These samples were analyzed in reference to a Phillips Petroleum lab standard AER. The following computation is made to convert to an industrial standard PDB:

$$\delta C^{13}{}_{AER} - (-27.32) = \delta C^{13}{}_{PDB}.$$

Table I gives the results of nine experimentally valid (selected) data points obtained using the described system.

TABLE 1

| Sample | $\delta C^{13}$ (AER) | $2\sigma$* |
|---|---|---|
| 1 | 2.017 | 0.006 |
| 2 | 1.711 | 0.011 |
| 3 | 1.567 | 0.037 |
| 4 | 1.421 | 0.013 |
| 5 | 1.538 | 0.045 |
| 6 | 1.677 | 0.009 |
| 7 | 1.600 | 0.022 |
| 8 | 1.371 | 0.032 |
| 9 | 1.553 | 0.037 |

Average $\delta C^{13} = 1.61 \pm 0.18$
*Two standard deviations

The average $\delta C^{13}$ obtained using the described method suggests that it can be used to obtain isotope ratios which are within tolerances acceptable for geological interpretation. The results are statistically comparable to results obtained using a Craig combustion system.

EXAMPLE 2

Figure 3:
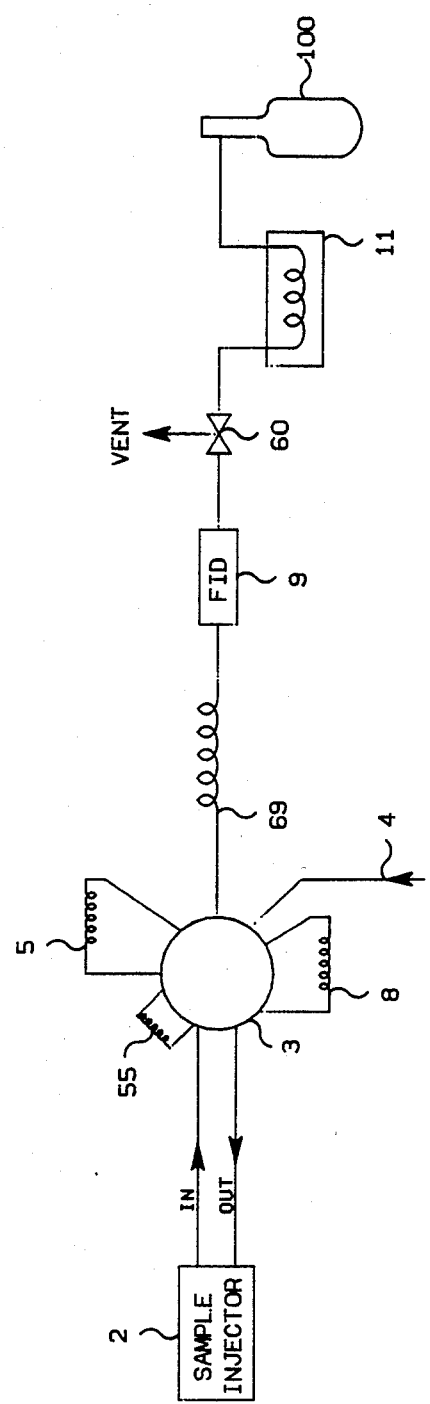
FIG. 3 is a schematic diagram of the method and apparatus according to a second embodiment of the invention.

A second series of runs was done using an alternate apparatus including a Sigma 1B (Perkin-Elmer) microprocessor-controlled gas chromatograph and a Micromass ®903 triple collector mass spectrometer. The gas sample inlet injection system for the gas chromatograph comprises a 1 cc volume of 1/16" stainless steel tubing feeding an 10-port Valco ® valve. The sample loop can be evacuated to process less than atomspheric samples. The sample gas collecting system is similar to that in Example 1, except that the effluent line from the FID to the vent valve is heated to about 110° C. The apparatus is connected as illustrated in FIG. 3.

A sample of NPGA Lot 36 in a 1 cc subsamples was fed by means of the gas inlet means 2 to the valve 3 and sample loop 55. The composition of the sample is shown in Table 2. Helium carrier gas flow was 30 cc/min. The sample was passed through a first gas chromatographic column 5 in an oven maintained at 40° C. The GC column contained phenylisocyanate on Porasil ® C 80/100 mesh packing. Components of the sample above $C_4$ were delayed in the column while propane ($C_3$) and lighter components eluted through to the second GC column 8. From the time of injection of the sample and until just prior to elution of the components from the first column, the FID output valve 60 was in the vent position to permit removal of water generated by the FID. Just prior to elution of the low molecular weight components of interest from the first column, the detector output valve was changed to the cold trap position. The eluted gases were passed to the second chromatographic column, having the same packing material as the first chromatographic column. After elution of the peaks of interest from the first column, the carrier flow was reversed through the first column to flush the undesired gases from the column.

TABLE 2

| Component | Volume % |
|---|---|
| He | 0.49 |
| $O_2$ | 0.01 |
| $N_2$ | 5 |
| $CO_2$ | 1.08 |
| $C_1$ | 70.16 |

TABLE 2-continued

| Component | Volume % |
|---|---|
| $C_2$ | 9.08 |
| $C_3$ | 6.05 |
| $C_3^=$ | 0.02 |
| $iC_4$ | 3.06 |
| $nC_4$ | 3.02 |
| $iC_5$ | 0.99 |
| $nC_5$ | 1.04 |

The eluted and separated gases from the second column were passed in seriatum to the FID 9 maintained at 125° C. and standard flow rates. In the detector, each hydrocarbon component in turn was combusted in an oxygen/hydrogen atmosphere to $CO_2$ and water, which were passed to nitrogen cold trap 11 for subsequent $CO_2$—$H_2O$ separation. The separated $CO_2$ was passed to the mass spectrometer via a sample vessel 100. A glass bead column 69 was placed between the second column 8 and detector 9 to eliminate flame blow out resulting from valve switching. Table 3 gives the results of isotopic analysis of the eight different subsamples analyzed for carbon dioxide from methane for each sample.

TABLE 3

| Sample | $\delta C^{13}$ (AER) | $2\sigma^*$ |
|---|---|---|
| 1 | −1.837 | .053 |
| 2 | −1.921 | .040 |
| 3 | −1.909 | .057 |
| 4 | −1.190 | .055 |
| 5 | −1.947 | .066 |
| 6 | −1.812 | .058 |
| 7 | −2.071 | .065 |
| 8 | −1.715 | .047 |

Average $\delta C^{13}$ = −1.8 ± .25

Variations in the $\delta C^{13}$ values for the above analysis were traced to a leaking FID. Combustion efficiency (conversion of methane to carbon dioxide) was approximately 80% during the leakage. No runs using this standard have been made since elimination of leaks, but a 95% combustion efficiency has been observed with other samples.

The $\delta C^{13}$ value of 1.61 from example 1 would predict that the gas source was directed more towards a non-marine origin. This particular value fell within a range between non-marine and marine but was more toward non-marine.

The $\delta C^{13}$ value of −1.8 from example 2 however would predict that the sample source was directed to a marine origin. These values along with other information can be used to evaluate and predict reservoir potentials.

I claim:

1. A method comprising:
   introducing a sample of matter containing an isotope of interest selected from isotopes of carbon and sulfur into an analytical detector selected from a flame ionization detector and a flame photometric detector operative to combust the sample and to detect a property representative of the presence of carbon or sulfur of the sample or a combustion product thereof, and producing combustion product comprising at least one of carbon dioxide and sulfur dioxide containing the isotope of interest; and
   passing at least the isotope of interest portion of the combustion product to a mass spectrometer operative to make a quantitative isotopic analysis of the isotope of interest and producing an output from the mass spectrometer representative of the quantitative isotopic analysis of the isotope of interest.

2. The method of claim 1 in which the analytical detector is a flame ionization detector operative to detect a property of the sample representative of its content of a substance selected from methane, ethane and propane.

3. The method of claim 1 in which the sample is selected from natural gas, petroleum, soil gas, shale, coal and constituents of these.

4. The method of claim 1 which further comprises passing a gaseous mixture through a gas chromatography column and separating the mixture into at least two constituents, one of which is the sample containing the isotope of interest.

5. The method of claim 1 in which the analytical detector is a flame ionization detector and the isotope of interest is carbon 13.

6. The method of claim 1 in which the analytical detector is a flame photometric detector and the isotope of interest is sulfur 34.

7. The method of claim 6 which further comprises determining from the isotopic analysis a property of the sample related to its geological history.

8. The method of claim 1 in which the sample of matter has a volume of about 1 cc to about 25 cc at STP.

9. The method of claim 8 in which the sample is a pyrolysis product of a solid material.

10. The method of claim 8 which further comprises passing a gaseous mixture through a gas chromatography column and separating the mixture into at least two constituents, one of which is the sample containing the isotope of interest.

11. The method of claim 10 in which the sample is passed to the analytical detector in a carrier gas and the combustion product containing the isotope of interest is concentrated with respect to the carrier gas prior to introduction of the combustion product into the mass spectrometer.

12. Apparatus for analyzing a sample of matter for an isotope of interest selected from isotopes of carbon and sulfur, the apparatus comprising:
   an analytical detector selected from a flame ionization detector and a flame photometric detector operative to convert a sample into a product comprising the isotope of interest and to detect a property representative of the presence of carbon or sulfur of an amount of an introduced material within the range of about 1 cc to about 25 cc at STP;
   a mass spectrometer having an inlet in flow communication with the analytical detector and operative to make a quantitative isotopic analysis of the isotope of interest.

13. The apparatus of claim 12 in which the mass spectrometer is an isotope ratio mass spectrometer.

14. The apparatus of claim 13 which further comprises a chromatography column having an outlet in flow communication with the analytical detector.

15. The apparatus of claim 12 in which the analytical detector is a flame ionization detector having an outlet for combustion products in flow communication with the inlet of the mass spectrometer via means to concentrate the combustion products relative to a carrier gas.

16. The apparatus of claim 15 in which the combustion product concentration means is a glass jet separator.

17. The apparatus of claim 14 which further comprises means to remove water vapor from combustion products of the analytical detector.

18. The apparatus of claim 12 which comprises:
- a gas chromatography column having an inlet and an outlet;
- means to introduce a gaseous sample in a quantity of about 1 cc to about 25 cc into the inlet of the gas chromatography column;
- a flame ionization detector having a sample inlet and a combustion product outlet, the inlet being in flow communication with the outlet of the gas chromatography column;
- an isotope ratio mass spectrometer having an inlet in flow communication with the outlet of the flame ionization detector; and
- means to remove water from a gas flowing from the outlet of the flame ionization detector to the inlet of the mass spectrometer.

19. The apparatus of claim 18 further comprising means for carrier gas introduction and means for reduction of carrier gas concentration between the outlet of the flame ionization detector and the mass spectrometer.

* * * * *

UNITED STATES PATENT AND TRADEMARK OFFICE
CERTIFICATE OF CORRECTION

PATENT NO. : 4,517,461

DATED : May 14, 1985

INVENTOR(S) : John A. Crandall

It is certified that error appears in the above-identified patent and that said Letters Patent is hereby corrected as shown below:

On the title page insert,

-- 73 Assignee: Phillips Petroleum Company
Bartlesville, Okla. --.

Column 8, claim 5, line 1, "1" should read --- 4 ---.
Column 8, claim 6, line 1, "1" should read --- 4 ---.
Column 8, claim 7, line 1, "6" should read --- 5 ---.

Signed and Sealed this

Twenty-ninth Day of April 1986

[SEAL]

Attest:

DONALD J. QUIGG

Attesting Officer

Commissioner of Patents and Trademarks